United States Patent [19]

Bernauer et al.

[11] 4,234,736
[45] Nov. 18, 1980

[54] ANTIANDROGENIC AND SCHISTOSOMICIDAL IMIDAZOLIDINE DERIVATIVES

[75] Inventors: Karl Bernauer, Oberwil; Helmut Link, Basel; Harro Stohler, Binningen, all of Switzerland

[73] Assignee: Hoffmann-La Roche Inc., Nutley, N.J.

[21] Appl. No.: 954,071

[22] Filed: Oct. 24, 1978

[30] Foreign Application Priority Data

| Oct. 28, 1977 | [LU] | Luxembourg | 78407 |
| Oct. 28, 1977 | [LU] | Luxembourg | 78408 |
| May 19, 1978 | [CH] | Switzerland | 5465/78 |
| May 19, 1978 | [CH] | Switzerland | 5466/78 |
| Sep. 7, 1978 | [CH] | Switzerland | 9407/78 |

[51] Int. Cl.³ .................. C07D 233/72; C07D 233/88
[52] U.S. Cl. ................................. 548/314; 424/273 R
[58] Field of Search .................... 548/314; 424/273 R

[56] References Cited

U.S. PATENT DOCUMENTS

| 3,134,663 | 5/1964 | Kroll | 548/314 |
| 3,668,217 | 6/1972 | Fujinami et al. | 548/314 |
| 3,676,456 | 7/1972 | Gruenfeld | 548/314 |
| 3,846,441 | 11/1974 | Mine et al. | 548/314 |
| 3,960,883 | 6/1976 | Hubele et al. | 548/314 |
| 4,044,021 | 8/1977 | Hanifin et al. | 548/314 |
| 4,097,578 | 6/1978 | Perronnet et al. | 548/314 |

FOREIGN PATENT DOCUMENTS

| 629779 | 10/1963 | Belgium | 548/314 |
| 1915689 | 10/1969 | Fed. Rep. of Germany | 548/314 |
| 1958183 | 6/1970 | Fed. Rep. of Germany . | |
| 2441601 | 3/1975 | Fed. Rep. of Germany . | |
| 2649925 | 5/1977 | Fed. Rep. of Germany . | |
| 2002196 | 10/1969 | France | 548/314 |
| 997037 | 6/1965 | United Kingdom . | |

OTHER PUBLICATIONS

Lombardino et al. J. Med. Chem. 1964, vol. 7, pp. 97–101.

*Primary Examiner*—Alan L. Rotman
*Assistant Examiner*—Natalia Harkaway
*Attorney, Agent, or Firm*—Jon S. Saxe; Bernard S. Leon; William M. Farley

[57] ABSTRACT

Imidazolidine derivatives, as well as processes for their preparation, which have antiandrogenic and schistosomicidal activity.

1 Claim, No Drawings

ANTIANDROGENIC AND SCHISTOSOMICIDAL IMIDAZOLIDINE DERIVATIVES

SUMMARY OF THE INVENTION

This invention discloses urea derivatives of the formula

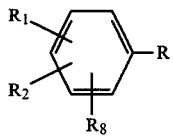   I where $R_1$ is halogen, trifluoromethyl, nitro or lower alkoxy, $R_2$ is hydrogen, halogen, trifluoromethyl, nitro or lower alkoxy and $R_8$ is hydrogen, halogen or trifluoromethyl, with $R_1$, $R_2$ and $R_8$ in the meta- or para-position relative to R; and where R is either

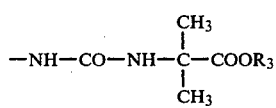  (a)

or

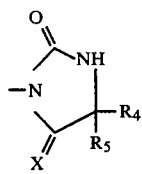  (b)

where $R_3$ is lower alkyl, X is oxygen or imino, $R_4$ is lower alkyl and $R_5$ is hydrogen or lower alkyl; with the provisos that (A) where $R_8$ is hydrogen and R is (b) and both $R_4$ and $R_5$ are methyl, then $R_1$ is halogen, trifluoromethyl or lower alkoxy and $R_2$ is hydrogen, halogen, trifluoromethyl or lower alkoxy; and (B) where R is (b) and the residue

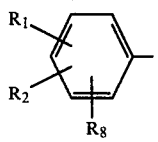

is selected from the group consisting of

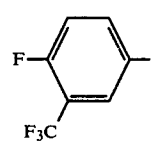

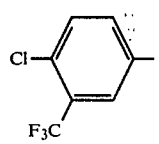

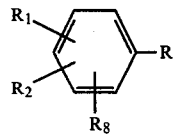

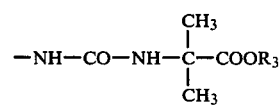

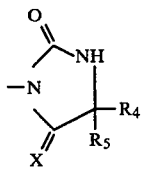

then $R_5$ must be hydrogen or alkyl of from 2 to 4 carbon atoms.

The compounds are active as antiandrogenic and/or schistosomicidal agents. Thus, this invention is also directed to pharmaceutical compositions containing these compounds as the active ingredients, as well as methods for use of these compositions as such agents.

DETAILED DESCRIPTION OF THE INVENTION

This invention is directed to compounds which are derivatives of urea having the formula

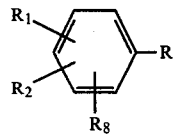   I where $R_1$ is halogen, trifluoromethyl, nitro or lower alkoxy, $R_2$ is hydrogen, halogen, trifluoromethyl, nitro or lower alkoxy and $R_8$ is hydrogen, halogen or trifluoromethyl, with $R_1$, $R_2$ and $R_8$ in the meta- or para-position relative to R; and where R is either

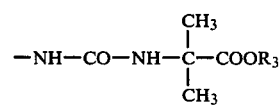  (a)

or

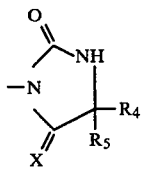  (b)

where $R_3$ is lower alkyl, X is oxygen or imino $R_4$ is lower alkyl and $R_5$ is hydrogen or lower alkyl;
with the provisos that (A) when $R_8$ is hydrogen and R is (b) and both $R_4$ and $R_5$ are methyl, then $R_1$ must be halogen, trifluoromethyl or lower alkoxy and $R_2$ must be hydrogen, halogen, trifluoromethyl or lower alkoxy and (B) when R is (b) and

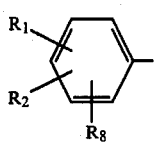

is selected from the group consisting of

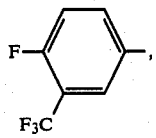

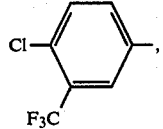

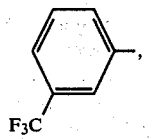

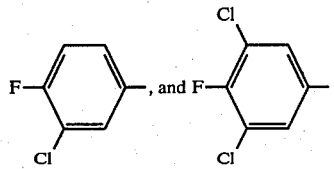

then R$_5$ must be hydrogen or alkyl of from 2 to 4 carbon atoms.

Some of the urea derivatives of the formula I are novel compounds and are likewise the object of the invention. These are the compounds of the formula

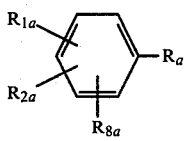

Ia in which R$_{1a}$ is halogen, trifluoromethyl, nitro or lower alkoxy, R$_{2a}$ is hydrogen, halogen, trifluoromethyl, nitro or lower alkoxy and R$_{8a}$ is hydrogen, halogen or trifluoromethyl, with R$_{1a}$, R$_{2a}$ and R$_{8a}$ in the meta- or para-position relative to R$_a$; and where, R$_a$ is either

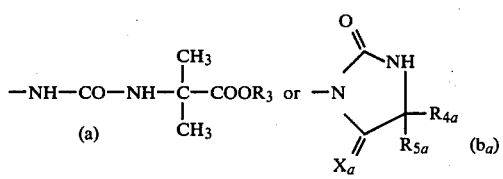

wherein R$_3$ is lower alkyl, X$_a$ is oxygen or imino, R$_{4a}$ is lower alkyl and R$_{5a}$ is hydrogen or lower alkyl;
with the provisos that
(A) when R$_{8a}$ is hydrogen and R$_a$ is (b$_a$) and both R$_{4a}$ and R$_{5a}$ are methyl, then R$_{1a}$ is halogen, trifluoromethyl or lower alkoxy and R$_{2a}$ is hydrogen, halogen, trifluoromethyl or lower alkoxy;

(B) when R$_a$ is (b$_a$) and

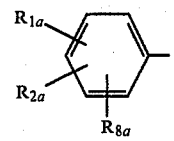

is selected from the group consisting of

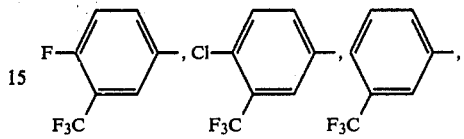

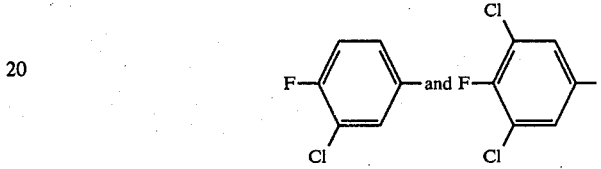

R$_{5a}$ is hydrogen or alkyl of from 2 to 4 carbon atoms and
(C) when R$_a$ is (b$_a$), and X$_a$ is oxygen then

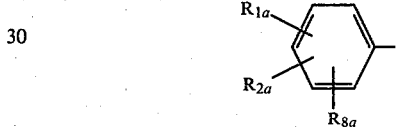

must be selected from the group consisting of

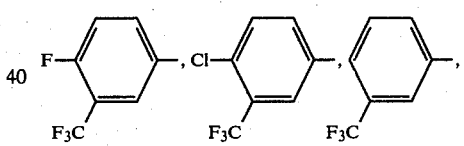

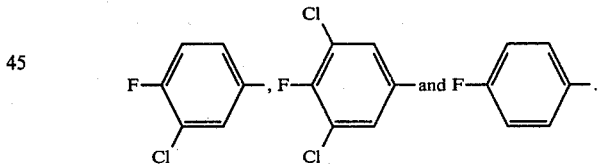

As used in this specification, the term "lower alkyl" means a straight or branched-chain alkyl group containing up to four carbon atoms such as methyl, ethyl, n-propyl, isopropyl, n-butyl, isobutyl, sec.-butyl and t-butyl. The term "lower alkoxy" means a straight or branched-chain alkoxy group containing up to four carbon atoms such as methoxy, ethoxy, n-propoxy, isopropoxy, n-butoxy, isobutoxy, sec.-butoxy and t-butoxy. The term "halogen" means fluorine, chlorine, bromine or iodine.

In addition substituents R$_1$ or R$_2$ are preferably in the 3- or 4-position on the phenyl ring and the substituent R$_8$ is preferably in the 5-position on the ring.

Those novel urea derivatives of the formula Ia where R$_a$ is (b$_a$) and, in particular, when X$_a$ is oxygen, i.e. a hydantoin derivative of the formula Ia, are preferred because of their antiandrogenic and schistosomicidal action.

The novel urea derivatives of the formula Ia in which $R_{1a}$ is chlorine, fluorine or trifluoromethyl, $R_{2a}$ is hydrogen, chlorine, fluorine or trifluoromethyl, $R_3$ is methyl, $R_{8a}$ is hydrogen, chlorine, fluorine or trifluoromethyl and $R_a$ is 5,5-dimethyl-3-hydantoyl are preferred because of their antiandrogenic action. A novel compound of the formula Ia which is especially preferred because of its antiandrogenic action is N-[(3-trifluoromethyl-4-chlorophenyl)-carbamoyl]-2-methylalanine methyl ester.

Those novel urea derivatives of the formula Ia where $R_{1a}$ is halogen, trifluoromethyl or nitro, $R_{2a}$ is hydrogen, halogen, trifluoromethyl or nitro, $R_{4a}$ and $R_{5a}$ are methyl and $R_{8a}$ is hydrogen are schistosomicidally active. Those compounds wherein $R_{1a}$ is chlorine, fluorine or trifluoromethyl, $R_{2a}$ is hydrogen, chlorine, fluorine or trifluoromethyl, $R_3$ is methyl, $R_{8a}$ is hydrogen, and $R_a$ is 5,5-dimethyl-3-hydantoyl are especially preferred because of their schistosomicidal action. Especially preferred schistosomicidally active novel compounds of the formula I are N-[(3-trifluromethyl-4-chlorophenyl)-carbamoyl]-2-methylalanine methyl ester and 3-(4-fluoro-phenyl)-5,5-dimethyl-hydantoin.

The novel urea derivatives of formula Ia can be prepared by the following procedures.

A. Preparation of a compound of formula Ia wherein $R_a$ is (a)

1. A compound of the formula

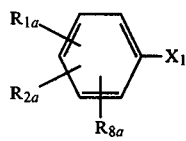

II is reacted, under anhydrous conditions, with a compound of the formula

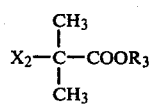

III in which $R_{1a}$, $R_{2a}$, $R_{8a}$ and $R_3$ have the above significance and one of $X_1$ and $X_2$ is amino and the other is the isocyanate group —NCO.

The anhydrous reaction of the compounds of formulas II and III is carried out either without solvents, i.e. by means of a melt, or by warming the starting compounds in an inert, anhydrous solvent, e.g. tetrahydrofuran, ether, dioxan, benzene or toluene. The reaction temperature is preferably in the range of about 0°–120° C. If the reaction is carried out in a melt, it must be noted that relatively high temperatures or relatively long reaction times lead to cyclization with formation of the corresponding hydantoin. Thus, the reaction should be monitored by, for example, thin-layer chromatography, to avoid the cyclization.

2. A compound of the formula

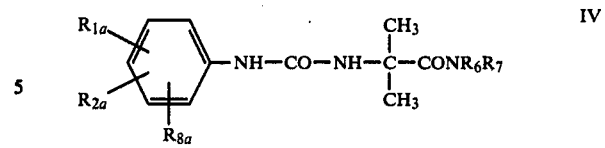

IV in which $R_{1a}$, $R_{2a}$ and $R_{8a}$ have the significance given above and $R_6$ and $R_7$ both are lower alkyl, is subjected to alcoholysis using an alcohol of the formula $R_3OH$, wherein $R_3$ has the same significance as above.

Compounds of formula IV are prepared by reacting a substituted benzhydroxamic acid of the general formula

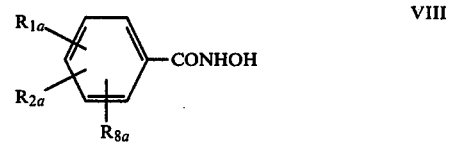

VIII in which $R_{1a}$, $R_{2a}$ and $R_{8a}$ have the same significance as above, with an azirine derivative of the general formula

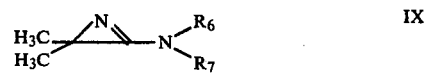

IX in which $R_6$ and $R_7$ have the same significance as given above. The reaction is carried out in an inert solvent, such as tetrahydrofuran, ether or dioxan, at room temperature or with slight warming, e.g. to 50° C.

Alcoholysis of an amide of formula IV is carried out using a lower alkanol, preferably methanol or ethanol, and leads to the formation of carboxylic acid esters of formula I wherein $R_a$ is (a). The alcoholysis is preferably carried out under acidic, e.g. with mineral acid, conditions, as for example, in methanolic or ethanolic hydrochloric acid. The reaction is preferably carried out at room temperature but, if desired, it can be increased to the boiling temperature of the reaction mixture.

3. A compound of the formula

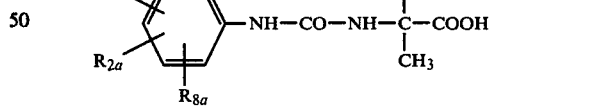

Ic in which $R_{1a}$, $R_{2a}$ and $R_{8a}$ have the same significance as given above,
is esterified with compounds which supply lower alkyl groups.

The esterification of the carboxylic acid of formula Ic leads to compounds of formula Ia wherein $R_a$ is (a). The esterification is carried out in a manner known per se by treatment with a lower alkanolic mineral acid, e.g. methanolic hydrochloric acid, with a lower alkyl halide, e.g. methyl iodide, and an alkali metal carbonate or bicarbonate in a solvent, such as dimethylformamide, or with diazomethane in an ethereal solvent, such as ether, tetrahydrofuran or dioxan. The esterification temperature is, in general, in the range of about 0°–50° C.

B. Preparation of a compound of formula Ia wherein R is (ba) and X is oxygen

1. A compound of the formula

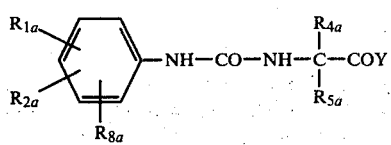

in which $R_{1a}$, $R_{2a}$, $R_{4a}$, $R_{5a}$ and $R_{8a}$ have the same significance as given above and Y is $-OR_{30}$ or $-NR_6R_7$, wherein $R_6$ and $R_7$ have the same significance and $R_{30}$ is hydrogen or lower alkyl, is cyclized.

The amides or esters of formula V are prepared by procedures analogously to those used in the preparation of the amides of formula IV or of the esters of formula Ia, from the compounds II and III. For the preparation of a carboxylic acid of the formula V, an amide of formula V can be dissolved in an inert organic solvent, such as, e.g. methanol or ethanol, and the solution can be treated with an aqueous alkali, e.g. caustic soda solution or caustic potash solution, at a temperature between room temperature and the boiling point of the reaction mixture. The corresponding carboxylic acid of the formula Ia is obtained in the customary manner by neutralization of the carboxylic acid salt formed by, for example, using a mineral acid.

The cyclization of the starting amides or esters of formula V leads to hydantoin derivatives of formula Ia, and in particular those wherein $R_a$ is $(b_a)$ and $X_a$ is oxygen. This cyclization is carried out, e.g., under the conditions of acid hydrolysis, preferably by treatment with an aqueous mineral acid, such as aqueous hydrochloric acid. The acid hydrolysis of amides of formula V is advantageously carried out in an inert organic solvent, e.g. tetrahydrofuran or dioxan, at about room temperature. The hydrolysis can also be carried out at higher temperatures, e.g. up to the boiling point of the reaction mixture. The cyclization of esters of formula V is preferably carried out with a water-miscible solvent, such as acetone, methyl ethyl ketone, tetrahydrofuran, dimethoxyethane or dioxan. A preferred cyclization agent is 6-N aqueous hydrochloric acid and acetone in a weight ratio of about 1:1. The preferred reaction temperature is the boiling temperature of the reaction mixture. Lower reaction temperatures, e.g. down to room temperature, with appropriately longer reaction times, can also be used. The starting esters of the formula V can also be cyclized by warming without solvents, i.e. by means of a melt. The temperature range for this melt reaction is preferably from about 100° to about 200° C. and, especially, from about 120° to about 160° C. In a preferred embodiment, the cyclization is carried out by mixing compounds of formulas II and III to form the starting esters of the formula V. Then, by selecting a proper reaction time and/or reaction temperature, the reaction will proceed to the desired cyclization product, i.e. the hydantoin of the formula Ia, without isolation of the intermediate formed, i.e. an ester of formula V. The reaction can be followed, for example, by thin-layer chromatography.

2. A compound of the formula

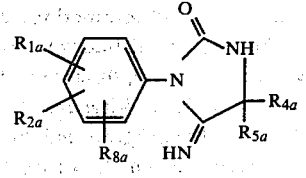

in which $R_{1a}$, $R_{2a}$, $R_{8a}$, $R_{4a}$ and $R_{5a}$ have the significance as noted above is subjected to hydrolysis.

The hydrolysis of the imino-imidazolidinone derivatives of formula Ib form the corresponding hydantoins of the formula Ia, i.e. wherein $R_a$ is $(b_a)$ and $X_a$ is oxygen. The hydrolysis can be carried out, optionally with the addition of an inert solvent, by treatment with, e.g., a mineral acid, such as hydrochloric acid, at a temperature between room temperature and the boiling point of the reaction mixture.

C. Preparation of a compound of formula Ia wherein $R_a$ is $(b_a)$ and $X_a$ is imino A compound of the formula

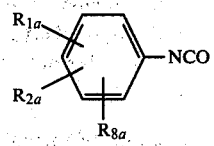

in which $R_{1a}$, $R_{2a}$ and $R_{8a}$ have the same significance as above, is reacted, under anhydrous conditions, with a compound of the formula

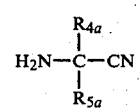

in which $R_{4a}$ and $R_{5a}$ have the same significance as above.

The anhydrous reaction of the starting compounds of formulas VI and VII forms imino-imidazolidinone derivatives of formula Ia, i.e. wherein $R_a$ is $(b_a)$ and $X_a$ is imino. The reaction can be carried out under the same conditions as the cyclization described above, using, as the starting materials, compounds of the formula II and III, i.e. by means of a melt. The starting compounds of the formulas II and III can also be heated with an ethereal solvent, e.g. with dioxan or dimethoxyethane.

D. Preparation of a compound of formula Ia wherein $R_{1a}$ and/or $R_{2a}$ are nitro A compound of the formula

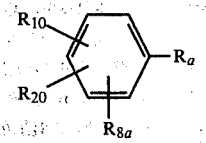

in which $R_a$ and $R_{8a}$ have the same significance as given above and both $R_{10}$ and $R_{20}$ have the same significances as given above for $R_{1a}$ and $R_{2a}$ with at least one of $R_{10}$ and $R_{20}$ being hydrogen, is nitrated.

The nitration of compounds of formula Id forms nitro derivatives of formula Ia wherein $R_{1a}$ and/or $R_{2a}$ are nitro. The compound of formula Id is nitrated in a manner known per se, e.g. by treatment with nitric acid, with nitric acid and sulphuric acid, with nitric acid and glacial acetic acid or acetic acid anhydride or with an alkali metal nitrate and sulphuric acid. The nitration is preferably carried out at a low temperature, for example at about 0° C. to room temperature.

Those compounds of formula I which are not novel compounds are prepared by procedures analogous to those described above for the novel compounds.

The compounds of formula I are partly crystalline, solid substances having good solubility in lower alkanols, such as methanol or ethanol, dimethyl sulphoxide, dimethylformamide and hexamethylphosphoric acid triamide, and partly also in chlorinated hydrocarbons, such as chloroform, methylene chloride and carbon tetrachloride. They are relatively sparingly soluble in ether, benzene and water.

The novel compounds of formulas IV and V are also part of this invention.

The various embodiments of the procedures for preparing the novel urea derivatives of formula I are detailed in the Examples.

The urea derivatives of this invention have antiandrogenic and/or schistosomicidal acivity. This can, thus, be used in novel antiandrogenic and/or schistosomicidal compositions.

For those compounds having antiandrogenic activity compositions can be prepared for the treatment of diseases associated with increased androgenic activity such as, e.g. acne, seborrhoea, hirsutism and adenoma of the prostate.

The preferred antiandrogenic compositions contain, as the active ingredient, a compound of formula I wherein R is (b) and, especially, where R is (b) and X is oxygen, i.e. a hydantoin derivative of formula I. The especially preferred antiandrogenic compositions are those which contain a compound of formula I in which $R_1$ is chlorine, fluorine or trifluoromethyl, $R_2$ is hydrogen, chlorine, fluorine or trifluoromethyl, $R_3$ is methyl, $R_8$ is hydrogen, chlorine, fluorine or trifluoromethyl and R is 5,5-dimethyl-3-hydantoyl.

Especially preferred compounds, on the basis of their antiandrogenic activity, are:

3-(3,4-Dichloro-phenyl)-5,5-dimethyl-hydantoin and

N-[(3-Trifluoromethyl-4-chlorophenyl)-2-carbamoyl]-2-methylalanine methyl ester.

The schistosomicidal active compositions of this invention can be used, e.g. for the prevention and therapy of bilharzioses. These compositions are those which contain, as the active ingredient a urea derivative of formula I wherein $R_1$ is halogen, trifluoromethyl or nitro, $R_2$ is hydrogen, halogen, trifluoromethyl or nitro, $R_4$ and $R_5$ are methyl and $R_8$ is hydrogen.

The preferred schistosomicidal compositions of this invention contain a compound of formula I wherein R is (b) and, in particular, where R is (b) and X is oxygen, i.e. a hydantoin derivative of formula I. Those schistosomicidal compositions containing compounds of formula I in which $R_1$ is chlorine, fluorine or trifluoromethyl, $R_2$ is hydrogen, chlorine, fluorine, or trifluoromethyl, $R_3$ is methyl, $R_8$ is hydrogen and R is 5,5-dimethyl-3-hydantoyl are especially preferred.

Especially preferred compounds, on the basis of their schistosomicidal action, are:

3-(4-Fluoro-phenyl)-5,5-dimethyl-hydantoin;

3-(3,4-Dichloro-phenyl)-5,5-dimethyl-hydantoin;

3-(4-Chloro-phenyl)-5,5-dimethyl-hydantoin and

N-[(3-Trifluoromethyl-4-chloro-phenyl)-carbamoyl]-methyl-alanine methyl ester.

The antiandrogenic and/or schistosomicidal compositions of this invention can be prepared using usual pharmaceutical procedures. For example, an active compound of formula I can be admixed with pharmaceutically acceptable carrier material. This carrier material can be pharmaceutically active or inactive, organic or inorganic. The carrier material can be suitable for enteral or parenteral administration. Examples of inactive carrier material include gelatin, lactose, starch, gum arabic, magnesium stearate, talc, vegetable oils, polyalkylene glycols, Vaseline and the like. Examples of pharmaceutically active carrier material include other therapeutically active substances.

The compositions can be prepared in solid form as, e.g. tablets or dragees, or in liquid form as, e.g. solutions suspensions or emulsions.

The carrier material also encompasses adjuvants such as preserving, stabilizing wetting or emulsifying agents, buffers and salts for varying the osmotic pressure.

The concentration of the active ingredient in the particular pharmaceutical dosage forms can range from about 10 mg. to about 500 mg. The actual amount of the active ingredient of formula I in a particular dosage form depends upon the particular individual requirements. For example, these compounds can be administered in dosages ranging from about 0.1 mg/kg. of body weight to about 50 mg./kg per os (p.o.) daily.

Dosage forms suitable for antiandrogenic use contain about 10–500 mg., preferably about 100 mg. of a compound of formula I. The dosage rate ranges from about 0.1 mg/kg. to about 10 mg/kg p.o. daily, preferably about 1 mg/kg p.o. daily. Such amounts can be administered daily for about 3–8 months, depending on the condition of the patient.

Dosage forms suitable for schistosomicidal use appropriately contain about 100–500 mg., preferably about 250 mg. of a compound of formula I. The dosage rate ranges from about 5 mg./kg. to about 50 mg/kg p.o. daily, preferably 25 mg/kg p.o. daily. This amount can be administered in a single dosage or in several smaller dosages depending on the requirements of the patient and the instructions of the physician. This dose can be administered on one day or on several successive days, according to the condition of the patient.

The antiandrogenic activity of the compositions of this invention can be determined in the following test:

10 mg. per kg of the composition together with 0.5 mg. per kg. of testosterone propionate are administered s.c. daily for 7 days to each of 5 male, sterilized rats. Two control groups of 5 rats each were also used. One control group received no treatment. The second control group received only 0.5 mg. per kg. of testosterone propionate.

Testosterone propionate causes an increase in weight in the ventral prostrate and the seminal vesicle. Thus, a decrease in weight in the ventral prostrate and the seminal vesicle when a composition containing a compound of formula I is given to the rats in combination with testosterone propionate is a measure of the antiandrogenic activity of that compound.

The results for two antiandrogenic compositions, each containing a different compound of formula I, are tabulated below.

TABLE I

| Compound | Ventral prostate mg | Seminal vesicle mg |
|---|---|---|
| Control | 17 ± 2 | 25 ± 2 |
| Testosterone propionate | 140 ± 11 | 88 ± 5 |
| 3-(3,4-Dichlorophenyl)-5,5-dimethyl-hydantoin + testosterone propionate | 36 ± 4 | 29 ± 2 |
| Control | 14 ± 1 | 24 ± 2 |
| Testosterone propionate | 121 ± 13 | 100 ± 9 |
| N-[(3-Trifluoromethyl-4-chlorophenyl)-carbamoyl]-2-methylalanine methyl ester + testosterone propionate | 61 ± 6 | 47 ± 11 |

The schistosomicidal activity of the compositions of this invention can be demonstrated in the following test.

Mice were infected subcutaneously with 60 cercariae of Schistosoma mansoni. 42 days after the infection, the animals were treated perorally on 5 successive days with the compositions to be tested 5–10 mice were used for each composition and dosage rate (mg/kg). 10 untreated mice serve as the control. The mice were autopsied either 6 days or 2–3 weeks after conclusion of the treatment. Worm pairs in mesenteric veins, the portal vein and the liver were removed and counted. The percent distribution of the worm pairs in mesenteric veins, the portal vein and the liver was calculated and the condition of the worms (living and dead) recorded. The schistosomicidal activity of the compositions containing a compound of formula I is shown both by an increased proportion of worms in the vessels of the liver and in the appearance of dead worms.

For the evaluation, the percentage proportions of living and dead worm pairs in the vessels of the liver both in infected, treated animals and in infected but untreated control animals were compared. The determination of the $VD_{50}$ (vermicidal dose 50%: the dose which kills 50% of the worm pairs) is carried out by the Probit method.

The results for four schistosomicidal compositions, each containing a different compound of formula I, are tabulated below.

TABLE II

| Compound | $VD_{50}$ mg/kg p.o. (administered 5 times) |
|---|---|
| 3-(4-Fluoro-phenyl)-5,5-dimethyl-hydantoin | 69 |
| N-[(3-Trifluoromethyl-4-chloro-phenyl)-carbamoyl]-2-methylalanine methyl ester | 74 |
| 3-(3,4-Dichloro-phenyl)-5,5-dimethyl-hydantoin | 58 |
| 3-(4-Chloro-phenyl)-5,5-dimethyl-hydantoin | 77 |

TABLE III

| Compound | $LD_{50}$ mg/kg p.o. |
|---|---|
| 3-(4-Fluoro-phenyl)-5,5-dimethyl-hydantoin | 600–1200 |
| N-[(3-Trifluoromethyl-4-chloro-phenyl)-carbamoyl]-2-methylalanine methyl ester | >5000 |
| 3-(3,4-Dichloro-phenyl)-5,5-dimethyl-hydantoin | 2500–5000 |
| 3-(4-Chloro-phenyl)-5,5-dimethyl-hydantoin | 1250–2500 |
| 3-(3-Trifluoromethyl-phenyl)-5,5-dimethyl-hydantoin | 625–1250 |

The following Examples illustrate the invention.

EXAMPLE 1

Preparation of N-[(4-chlorophenyl)-carbamoyl]-2-methylalanine methyl ester.

33 ml (0.255 mol) of 3-dimethylamino-2,2-dimethyl-2H-azirine were added, under an argon atmosphere, to 43.7 g (0.255 mol) of p-chlorobenzhydroxamic acid dissolved in 1300 ml of absolute tetrahydrofuran. The mixture was stirred at room temperature for four days. The resulting product which had precipitated was filtered off and recrystallized from tetrahydrofuran to yield 1-(4-Chlorophenyl)-3-[1-dimethylcarbamoyl)-1-methylethyl]-urea, melting point 216°–218° C.

Analysis Calc'd for $C_{13}H_{18}ClN_3O_2(\%)$: C,55.03; H,6.39; N,14.81; Cl,12.49: Found: C,55.07; H,6.53; N,14.74; Cl,12.67.

Using an analogous procedure 1-(4-nitrophenyl)-3-[1-dimethylcarbamoyl)-1-methyl-ethyl]-urea, m.p. 215° C. (dec.), can be prepared as the starting material.

23.5 g (83 mmol) of the 1-(4-chlorophenyl)-3-[1-dimethylcarbamoyl)-1-methylethyl]-urea dissolved in 1000 ml of absolute methanol was stirred for two days at room temperature with 7.5 ml (83 mmol) of methanolic hydrochloric acid. The mixture was then evaporated and 50 ml of water were added thereto. This residue was extracted several times with chloroform and the combined chloroform extracts were dried over sodium sulphate and evaporated. The residue was recrystallized from chloroform-hexane to yield N-[(4-chlorophenyl)-carbamoyl]-2-methylalanine methyl ester, m.p.-148°–150° C.

Analysis Calc'd for $C_{12}H_{15}ClN_2O_3(\%)$: C,53.24; H,5.58; N,10.35; Cl,13.10; Found: C,53.40; H,5.69; N,10.30; Cl,13.19.

EXAMPLE 2

Preparation of 3-(4-nitrophenyl)-5,5-dimethylhydantoin 300 ml of concentrated hydrochloric acid were added dropwise to a suspension of 33.8 g (115 mmol) of 1-(4-nitrophenyl)-3-[1-dimethylcarbamoyl)-1-methylethyl]-urea in 1000 ml of tetrahydrofuran using cooling with an ice bath. The resulting solution was stirred at room temperature for two days. The reaction mixture was then neutralized with sodium carbonate and extracted several times with chloroform. The chloroform extracts were dried over sodium sulphate and the chloroform was evaporated. The crude product was recrystallized from ether to yield 3-(4-Nitrophenyl)-5,5-dimethyl-hydantoin, m.p. 176°–177° C.

3-(4-Nitrophenyl-5,5-dimethylhydantoin was also prepared by the nitration of 17.0 g of 3-phenyl-5,5-dimethylhydantoin with 7.1 g of sodium nitrate in 160 ml. of concentrated sulfuric acid.

EXAMPLE 3

Preparation of N-[(4-chlorophenyl)-carbamoyl]-2-methylalanine, methyl ester.

A solution of 17.0 g (119 mmol) of 2-isocyanato-2-methylpropionic acid methyl ester in 150 ml of absolute tetrahydrofuran was added, over a 15 minute period to 15.1 g (119 mmol) of p-chloroaniline in 300 ml of absolute tetrahydrofuran. After refluxing the mixture for three days, the solution was evaporated to dryness. The product, after two recrystallizations from methylene chloride, was dried for 6 hours at 40° C., under greatly reduced pressure, to yield N-[(4-chlorophenyl)-carbamoyl]-2-methylalanine methyl ester, m.p. 147°–148° C.

Using analogous procedures the following compounds were prepared:

N-[(3-Chlorophenyl)-carbamoyl]-2-methylalanine methyl ester (after 2 days refluxing), m.p. 135°–136° C.;

N-[(3,4-Dichlorophenyl)-carbamoyl]-2-methylalanine methyl ester (after 2 days refluxing), m.p. 153°–154° C.;

N-[(4-Bromophenyl)-carbamoyl]-2-methylalanine methyl ester (after 2 days refluxing), m.p. 143°–145° C. and N-[(4-Fluorophenyl)-carbamoyl]-2-methylalanine methyl ester (after 1 day refluxing), m.p. 132° C.

EXAMPLE 4

Preparation of N-[(3-Trifluoromethyl-4-chlorophenyl)-carbamoyl]-2-methylalanine methyl ester.

9.75 g (50 mmol) of 5-amino-2-chlorobenzotrifluoride and 7.15 g (50 mmol) of 2-isocyanato-2-methylpropionic acid methyl ester were admixed and melted at 80° C. The melt was maintained at 80° C. for 30 minutes. The resulting product which was crystallized during the process, was recrystallized from isopropanol/methylene chloride and dried at 50° C. for 20 hours, under greatly reduced pressure, to yield N-[(3-Trifluoromethyl-4-chloro-phenyl)-carbamoyl]-2-methylalanine methyl ester, m.p. 141°–142° C.

Analysis Calc'd for $C_{13}H_{14}ClF_3N_2O_3$(%): C,46.10; H,4.17; N,8.27; Found: C,46.17; H,4.14; N,8.26.

Using analogous procedures, the following compounds were prepared:

N-[(4-Chlorophenyl)-carbamoyl]-2-methylalanine methyl ester (melt temperature—140° C., reaction time—10 minutes), m.p. 148°–150° C.;

N-[(4-Trifluoromethylphenyl)-carbamoyl]-2-methylalanine methyl ester (melt temperature—120° C., reaction time—60 minutes), m.p. 156° C. (sintering) 220° (decomp.);

N-[(4-Iodophenyl)-carbamoyl]-2-methylalanine methyl ester (melt temperature—90° C., reaction time—30 minutes), m.p. 148°–149° C.;

N-[(3-Nitro-4-chlorophenyl)-carbamoyl]-2-methylalanine methyl ester (melt temperature—100° C., reaction time—30 minutes), m.p. 142°–143° C. and N-[(3-Trifluoromethylphenyl)-carbamoyl]-2-methylalanine methyl ester (melt temperature—130° C., reaction time—120 minutes).

EXAMPLE 5

A solution of 17.2 g (67.5 mmol) of N-[(4-fluorophenyl)-carbamoyl]-2-methylalanine methyl ester in 150 ml of 6-N aqueous hydrochloric acid and 50 ml of acetone was warmed on a steam bath for 2 hours. The mixture was then concentrated. The product, which had precipitated was dried at 40°/15 Torr and then recrystallized from toluene. The recrystallized product was dried at 50° C. for 20 hours, under greatly reduced pressure, to yield 3-(4-fluorophenyl)-5,5-dimethylhydantoin, m.p. 166°–167° C.

Using analogous procedures, the following compound were prepared:

3-(4-Bromophenyl)-5,5-dimethylhydantoin, m.p. 172°–173° C.;

3-(4-Trifluoromethylphenyl)-5,5-dimethylhydantoin, m.p. 175°–176° C.;

3-(3-Nitro-4-chlorophenyl)-5,5-dimethylhydantoin, m.p. 165°–166° C.;

3-(3,4-Dichlorophenyl)-5,5-dimethylhydantoin, m.p. 193°–194° C. and 3-(4-Chlorophenyl)-5,5-dimethylhydantoin, m.p. 136°–137° C.

EXAMPLE 6

Preparation of 3-(4-nitrophenyl)-5,5-dimethylhydantoin.

17.0 g (83 mmol) of 3-phenyl-5,5-dimethylhydantoin were dissolved in 160 ml of concentrated sulphuric acid and 7.07 g (83 mmol) of sodium nitrate were slowly added with stirring, at 0° C. over a 40 minute period. After the addition was completed, maintained stirring at 0° C. was continued for 20 minutes with the reaction mixture. The mixture was allowed to warm to room temperature and stirring was continued for 4 hours. The mixture was then poured onto ice water and then extracted with methylene chloride. The extract was dried over sodium sulphate. The methylene chloride was evaporated and the resulting product was crystallized from methylene chloride/petroleum ether. The recrystallized product was dried for 16 hours, under greatly reduced pressure, to yield 3-(4-nitrophenyl)-5,5-dimethylhydantoin, m.p. 176°–177° C.

Analysis Calc'd for $C_{11}H_{11}N_3O_4$(%): C,53.01; H,4.45; N,16.86; Found: C,53.08; H,4.38; N,16.82.

EXAMPLE 7

Preparation of 3-(3-chloro-4-fluorophenyl)-5-methylhydantoin.

A mixture of 2.91 g (20 mmol) of 3-chloro-4-fluoroaniline and 3.01 g (21 mmol) of 2-isocyanato-propionic acid ethyl ester was maintained at 130°–140° C. for 9½ hours. The resulting product was crystallized from chloroform/methanol to yield 3-(3-chloro-4-fluorophenyl)-5-methyl-hydantoin, m.p. 174°–175.5° C.

Analysis Calc'd for $C_{10}H_8ClFN_2O_2$(%): C,49.50; H,3.32; N,11.55; Cl,14.61; Found: C,49.49; H,3.18; N,11.51; Cl,14.82.

EXAMPLE 8

Preparation of 3-(4-chloro-3-trifluoromethylphenyl)-5,5-diethylhydantoin.

An admixture of 6.65 g (30 mmol) of 4-chloro-3-trifluoromethylphenyl-isocyanate and 4.4 g (30 mmol) of 2-amino-2-ethyl-butyric acid methyl ester were heated to 100° C. and maintained at that temperature for 5 minutes. The resulting crude product, 2-(N-[(4-chloro-3-trifluoromethylphenyl)-carbamoyl]-amino)-2-ethyl-butyric acid methyl ester, was heated for 8 hours on a steam bath in a mixture of 200 ml of acetone and 200 ml of 6 N HCl. The mixture was cooled and then extracted with methylene chloride. The extract was dried over sodium sulphate and the methylene chloride was evaporated. The residue was crystallized from petroleum ether and then from methylene chloride/hexane to yield 3-(4-chloro-3-trifluoromethylphenyl)-5,5-diethylhydantoin, m.p. 86°–87° C.

Analysis Calc'd for $C_{14}H_{14}ClF_3N_2O_2$(%): C,50.24; H,4.22; N,8.37; Found: C,50.40; H,4.34; N,8.27.

EXAMPLE 9

Tablets containing a compound of formula I as the active ingredient were prepared from the following compositions:

| Ingredient | mg/tablet |
| --- | --- |
| Active compound of formula I | 100.0 |
| Lactose | 40.0 |
| Maize starch | 34.0 |
| Ethyl cellulose | 4.0 |
| Talc | 1.8 |
| Magnesium stearate | 0.2 |
| | 180.0 mg |

The compound of formula I was mixed with the lactose and maize starch. This mixture was granulated with a solution of the ethyl cellulose in 16 ml of methylene chloride. The granulate was dried at 40° C., mixed with the talc and magnesium stearate and pressed into tablets using standard tableting techniques.

| | |
| --- | --- |
| Weight of one tablet | 180 mg |
| Content of the compound of formula I in one tablet | 100 mg |

EXAMPLE 10

Tablets containing a compound of formula I as the active ingredient were prepared from the following composition.

| Ingredient | mg/tablet |
| --- | --- |
| Compound of formula I | 250.0 |
| Lactose | 100.0 |
| Maize starch | 85.0 |
| Ethyl cellulose | 10.0 |
| Talc | 4.5 |
| Magnesium stearate | 0.5 |
| | 450.0 mg |

The compound of formula I was mixed with the lactose and maize starch. This mixture was granulated with a solution of ethyl cellulose in 40 ml of methylene chloride. The granulate was dried at 40° C., mixed with the talc and magnesium stearate and pressed into tablets using standard tableting techniques.

| | |
| --- | --- |
| Weight of one tablet | 450 mg |
| Content of the compound of formula I in one tablet | 250 mg |

EXAMPLE 11

Capsules containing a compound of formula I as the active ingredient were prepared from the following compositions.

| Ingredient | mg/capsule |
| --- | --- |
| Compound of formula I | 100.0 |
| Lactose | 62.0 |
| Maize starch | 12.0 |
| Talc | 6.0 |
| | 180.0 mg |

The compound of formula I was homogeneously mixed with the lactose and maize starch. This mixture was passed through a sieve machine and then admixed with talc. The composition was then filled into gelatin capsules.

| | |
| --- | --- |
| Weight of filling in capsule | 180 mg |
| Content of compound of formula I in a capsule | 100 mg |

EXAMPLE 12

Capsules containing a compound of formula I as the active ingredient were prepared from the following composition.

| Ingredient | mg/capsule |
| --- | --- |
| Compound of formula I | 250.0 |
| Lactose | 155.0 |
| Maize starch | 30.0 |
| Talc | 15.0 |
| | 450.0 mg |

The compound of formula I was homogeneously mixed with the lactose and maize starch. The mixture was passed through a sieve machine and then admixed with talc. The composition was then filled into gelatin capsules.

| | |
| --- | --- |
| Weight of filling in capsule | 450 mg |
| Content of compound of formula I in a capsule | 250 mg |

We claim:

1. A compound of the formula

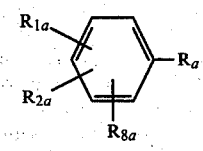

wherein

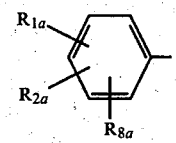

is selected from the group consisting of

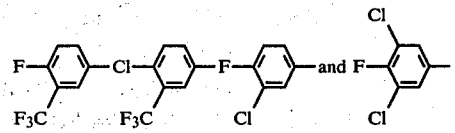

and $R_a$ is

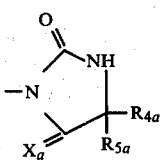

wherein $X_a$ is oxygen or imino, $R_{4a}$ is lower alkyl and $R_{5a}$ is hydrogen or alkyl of from 2 to 4 carbon atoms.

* * * * *